United States Patent
Lorusso et al.

(10) Patent No.: US 7,098,456 B1
(45) Date of Patent: Aug. 29, 2006

(54) METHOD AND APPARATUS FOR ACCURATE E-BEAM METROLOGY

(75) Inventors: Gian Francesco Lorusso, Fremont, CA (US); Paola De Cecco, Foster City, CA (US); Luca Grella, Gilroy, CA (US); David L. Adler, San Jose, CA (US); David Goodstein, San Francisco, CA (US); Chris Bevis, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 202 days.

(21) Appl. No.: 10/918,088

(22) Filed: Aug. 13, 2004

(51) Int. Cl.
*H01J 37/28* (2006.01)
*G01N 23/225* (2006.01)

(52) U.S. Cl. ...................... 250/310; 250/307
(58) Field of Classification Search .............. None
See application file for complete search history.

(56) References Cited

U.S. PATENT DOCUMENTS

| | | | | |
|---|---|---|---|---|
| 4,447,731 A | * | 5/1984 | Kuni et al. | 250/310 |
| 5,969,357 A | * | 10/1999 | Todokoro et al. | 250/310 |
| 6,373,053 B1 | * | 4/2002 | Choo et al. | 250/310 |
| 6,570,154 B1 | * | 5/2003 | Masnaghetti et al. | 250/310 |
| 6,646,737 B1 | | 11/2003 | Tortonese et al. | |

OTHER PUBLICATIONS

Luca Grella, et al., "Three Dimensional Simulation of SEM Imaging and Charging" 2001, Metrology, Inspection, and Process Control for Microlithography XV, Neal T. Sullivan, Editor, Proceeding of SPIE, vol. 4344.

Luca Grella, et al., "SEM Voltage Contrast Simulation" Jul. 1999, Part of the SPIE Conference on Charged Particle Optics IV, SPIE vol. 3777, Denver, CO.

Luca Grella, et al., "Simulations of SEM imaging and charging" 2004, Nuclear Instrument and Methods in Physics Research A 519, pp. 242-250.

Luc Grella, et al., "Simulations of Scanning Electron Microscopy Imaging and Charging of Insulating Structures" 2003, SCANNING vol. 25, pp. 300-308.

* cited by examiner

*Primary Examiner*—Jack I. Berman
(74) *Attorney, Agent, or Firm*—Okamoto & Benedicto LLP

(57) ABSTRACT

One embodiment disclosed relates to a method for accurate electron beam metrology. A substrate with a target feature is loaded into a scanning electron microscope. An electron beam is scanned over the target feature, and scattered electrons are detected therefrom. A characteristic of the target feature is measured by finding optimal values for parameters of a mathematical model which accounts for substrate charging effects. Principal component analysis may be used to advantageously result in reduced requirements for processing time and/or computational speed.

21 Claims, 18 Drawing Sheets

FIG. 2       200

- Suppose $x_1, x_2, \ldots, x_M$ are $N \times 1$ vectors

Step 1: $\bar{x} = \dfrac{1}{M} \sum\limits_{i=1}^{M} x_i$

Step 2: subtract the mean: $\Phi_i = x_i - \bar{x}$

Step 3: form the matrix $A = [\Phi_1 \ \Phi_2 \ \cdots \ \Phi_M]$ ($N \times M$ matrix), then compute:

$$C = \dfrac{1}{M} \sum_{n=1}^{M} \Phi_n \Phi_n^T = AA^T$$

(sample covariance matrix, $N \times N$, characterizes the *scatter* of the data)

Step 4: compute the eigenvalues of $C$: $\lambda_1 > \lambda_2 > \cdots > \lambda_N$ Step 5: compute the eigenvectors of $C$: $u_1, u_2, \ldots, u_N$

- Since $C$ is symmetric, $u_1, u_2, \ldots, u_N$ form a basis, (i.e., any vector $x$ or actually $(x - \bar{x})$, can be written as a linear combination of the eigenvectors):

$$x - \bar{x} = b_1 u_1 + b_2 u_2 + \cdots + b_N u_N = \sum_{i=1}^{N} b_i u_i$$

Step 6: (dimensionality reduction step) keep only the terms corresponding to the $K$ largest eigenvalues:

$$\hat{x} - \bar{x} = \sum_{i=1}^{K} b_i u_i \text{ where } K \ll N$$

- The representation of $\hat{x} - \bar{x}$ into the basis $u_1, u_2, \ldots, u_K$ is thus $$\begin{bmatrix} b_1 \\ b_2 \\ \ldots \\ b_K \end{bmatrix}$$

FIG. 6A

METHOD AND APPARATUS FOR ACCURATE E-BEAM METROLOGY

BACKGROUND OF THE INVENTION

1. Field of the Invention

The present invention relates to electron beam (e-beam) apparatus and metrology.

2. Description of the Background Art

As technology progresses in the semiconductor industry, the features of integrated circuit devices are being reduced to smaller and smaller sizes. Such reduction in feature size enables a greater density of devices to be manufactured on a semiconductor. However, increasingly smaller feature sizes require increasingly higher resolutions and accuracy in measurement, inspection, and review equipment.

One category of such equipment is based on scanning electron microscope (SEM) technology. In an SEM, a beam of electrons (an electron beam or e-beam) is scanned over a specimen, and the resulting electrons that are returned from the specimen surface are used to create an image of the specimen surface. In order to handle increasingly smaller feature sizes, it is desirable to increase the effective accuracy of SEM-based equipment used for feature measurement, substrate inspection, or defect review.

SUMMARY

One embodiment of the invention relates to a method for accurate electron beam metrology. A substrate with a target feature is loaded into a scanning electron microscope. An electron beam is scanned over the target feature, and scattered electrons are detected therefrom. A characteristic of the target feature is measured by finding optimal values for parameters of a mathematical model which accounts for substrate charging effects. Principal component analysis may be used to advantageously result in reduced requirements for processing time and/or computational speed.

BRIEF DESCRIPTION OF THE DRAWINGS

FIGS. 6A and 6B are diagrams depicting principal component analysis in accordance with an embodiment of the invention.

DETAILED DESCRIPTION

Figure 1:
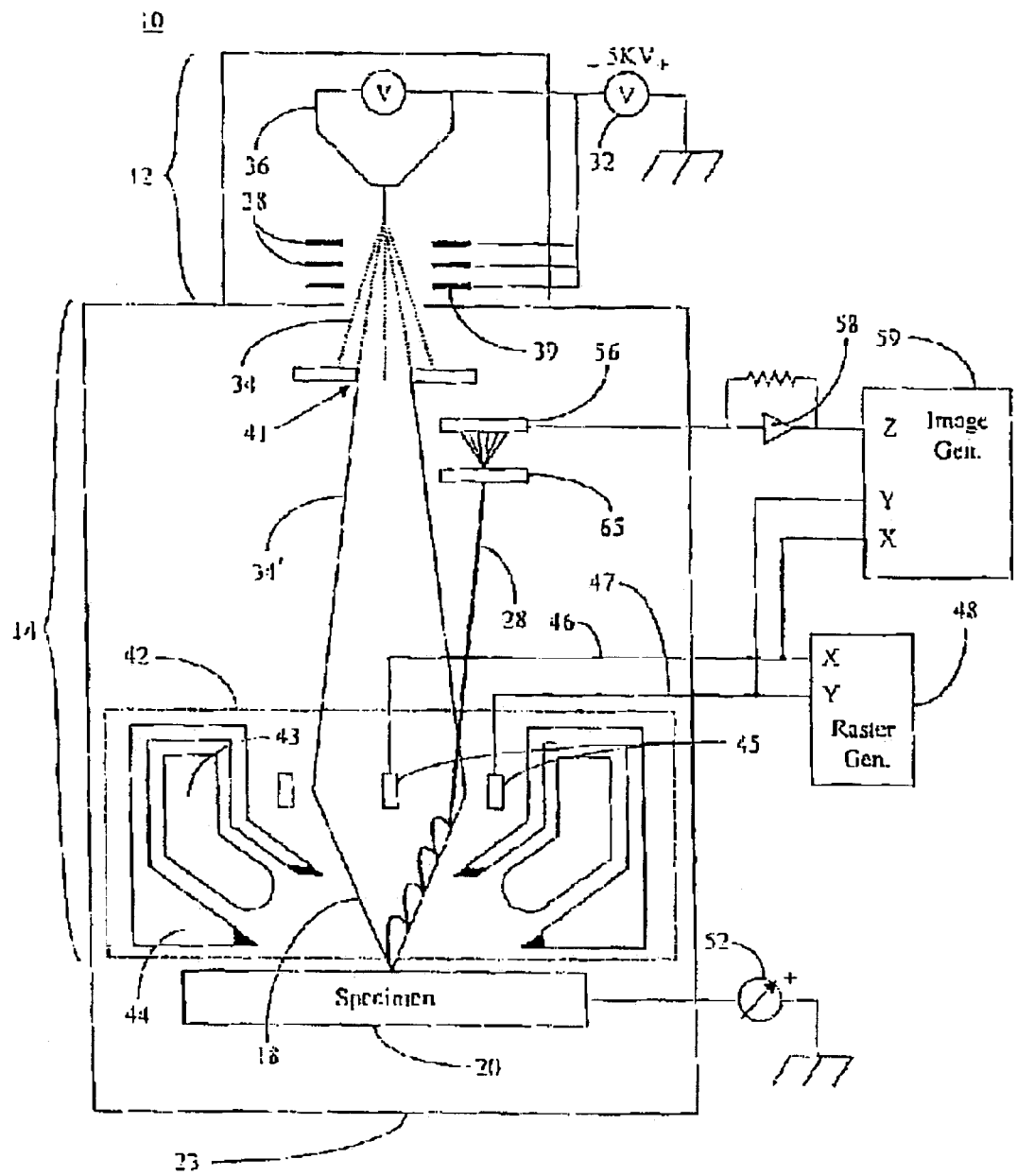
FIG. 1 is a schematic diagram of an example scanning electron beam apparatus with which the invention may be utilized.

FIG. 1 is a schematic diagram of an example scanning electron beam apparatus 10 with which the invention may be utilized. This example apparatus 10 is discussed for illustrative purposes. In other embodiments, the invention may be utilized with other types of electron beam apparatus having various specific configurations.

As shown here, the apparatus 10 includes an electron beam source 12 which produces an electron beam 34. One implementation that could be used includes an electron gun 36 that consists of a thermal field emitter (TFE) with the electrons accelerated by a surface field generated by power supply 32. Alternative electron gun embodiments could be employed. The electrons emitted by electron gun 36 are then, within beam source 12, directed through electrodes 38 and gun lens 39 (each also controlled by power supply 32) to form electron beam 34 that enters focusing column and lens assembly 14 to be directed to specimen 20. It should also be noted that electrodes 38 typically include both suppressor and extractor electrodes.

In focusing column and lens assembly 14, electron beam 34 passes through an aperture 41, reducing the beam current, for example, from approximately 300 pA to a range of 5 to 100 pA, and forming what is labeled electron beam 34' in FIG. 1. A larger electron beam current (e.g., 100 pA) is particularly useful for pattern recognition. That larger beam current also reduces the integration time to achieve a given signal-to-noise ratio for the image or linescan. Stated a little differently, there is a better signal-to-noise ratio for higher beam currents, however there is an improved image quality for lower beam currents.

Electron beam 34' then passes through objective lens 42, including magnetic coils 43 and pole pieces 44, that generate a strong magnetic field. That magnetic field is used to focus beam 34' to form electron beam 18 with a spot size of, for example, approximately 5 nm when directed at specimen 20. Additionally, the location of electron beam 18 is controlled with scan plates 45, located within the magnetic field created by coils 43 and pole pieces 44, with scan plates 45 powered by raster generator 48 to direct beam 18 in both the x and y directions across specimen 20 by signals on lines 46 and 47, respectively.

As beam 34' passes through the magnetic field of the objective lens 42 and plates 45, it is focused into beam 18 and directed onto the specimen 20. The spacing between column 14 (bottom of lens 42) and specimen 20 will typically be, for example, on the order of 2 mm. In addition, the specimen 20 is biased to a selected potential by a second power supply 52 (e.g., up to 5 VDC) to create an extremely large decelerating field for the primary electrons of beam 18 as they approach specimen 20. The result is that the "landing energy" of those electrons as they reach specimen 20 is therefore much lower than the energy with which they are provided by electron gun 36 and with which they travel through column and lens assembly 14. The electron beam of the illustrated implementation starts out from electron gun 36 with an energy level of, for example, 5000 eV, and travels through column and lens assembly 14 with that energy level essentially unchanged. As electron beam 18 exits lens 42, the decelerating field radiating from specimen 20, created by the bias of second power supply 52, substantially decelerates the electrons within beam 18 to the desired landing energy.

Secondary and/or backscatter electrons 28 are released as a result of the interaction of electron beam 18 with specimen 20 and are directed back toward lens 42. As electrons 28 are released, they spiral through lens 42 as a result of the magnetic field, and then travel toward detector 65 as they leave the field within lens 42. The electron signal received by detector 65 is then collected by collector plate 56 which in-turn generates a signal that is amplified by transimpedance amplifier 58 before being applied to image generator 59. Other input signals to image generator 59 are signals x and y from raster generator 48 on lines 46 and 47, respectively, to form a video signal representing an image of specimen 20, or selected portions thereof.

Figure 2:
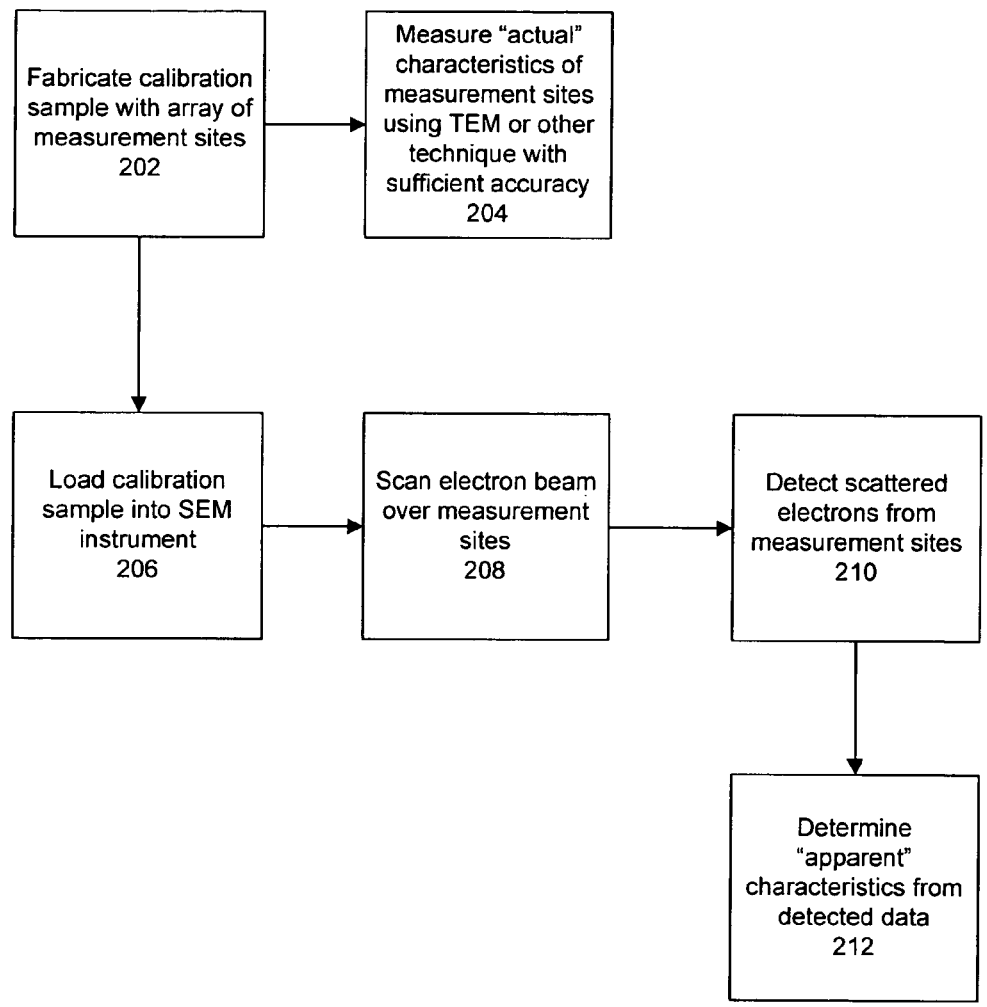
FIG. 2 is a flow chart depicting a method of obtaining calibration data in accordance with an embodiment of the invention.

FIG. 2 is a flow chart depicting a method 200 of obtaining calibration data in accordance with an embodiment of the invention. The method 200 includes fabricating a calibration specimen and determining "actual" and "apparent" characteristics thereof.

The calibration sample may be fabricated 202 so as to have an array of measurement sites. In one specific implementation, the calibration sample may be fabricated in a manner described in U.S. Pat. No. 6,646,737, entitled "Submicron dimensional calibration standards and method of manufacture and use," issued Nov. 11, 2003, to inventors Marco Tortonese et al., and assigned at issuance to KLA-Tencor Technologies of Milpitas, Calif. (the Tortonese patent). At each measurement site, there is at least one feature with at least one measurable characteristic. The measureable characteristic may comprise, for example, a line or trench width, or a dimension of a via. The measureable characteristic may also comprise profile information, such as, for example, the undercut angle of a line formed on a substrate.

Figure 3:
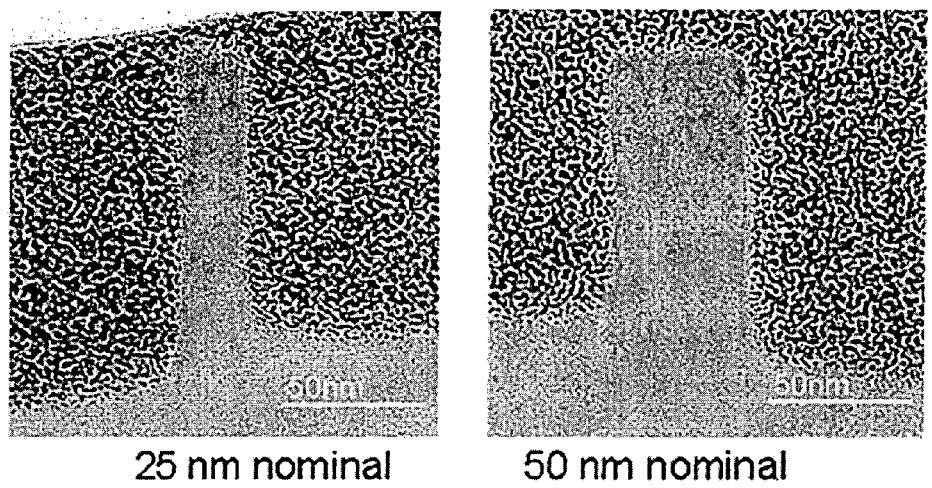
FIG. 3 depicts transmission electron microscope cross-sectional images of two lines.

The "actual" characteristics of the measurement sites of the calibration specimen are then measured 204 using transmission electron microscopy (TEM) or another technique with sufficient accuracy. For example, FIG. 3 depicts two lines of a calibration specimen as imaged in cross-section using TEM. The two lines shown have widths of approximately 25 nm and 50 nm.

Figure 4:
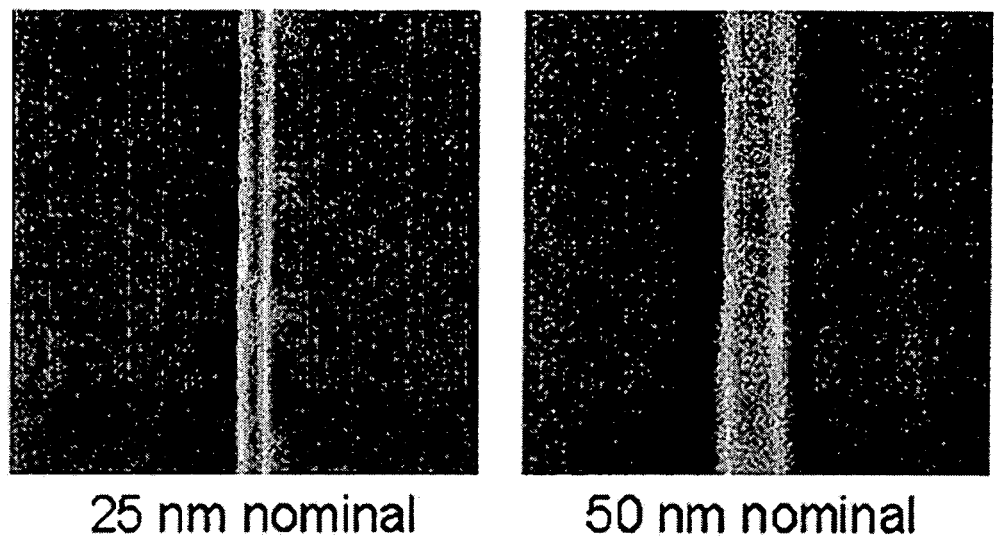
FIG. 4 depicts scanning electron microscope top view images of two lines.

The calibration sample is then loaded 206 into the specific scanning electron microscope (SEM) instrument being calibrated. The electron beam of the SEM is scanned 208 over the measurement sites, and electrons scattered therefrom are detected 210. These detected electrons may include secondary and/or backscattered electrons, depending on the specific operating conditions. For example, FIG. 4 depicts two lines of a calibration sample as imaged in top-view using an SEM. Again, the two lines shown have widths of approximately 25 nm and 50 nm.

From the detected data, the "apparent" characteristics are determined 212. These "apparent" characteristics are the characteristics as measured by the specific e-beam apparatus and the specific operating conditions of interest.

In accordance with an embodiment of the invention, a mathematical model is determined for the interaction of the electron beam and the measurement sites. The model uses various inputs, including, a set of properties of the specific SEM instrument, a set of properties of the measurement sites, and the "actual" and "apparent" measured characteristics from the calibration data.

Figure 5:
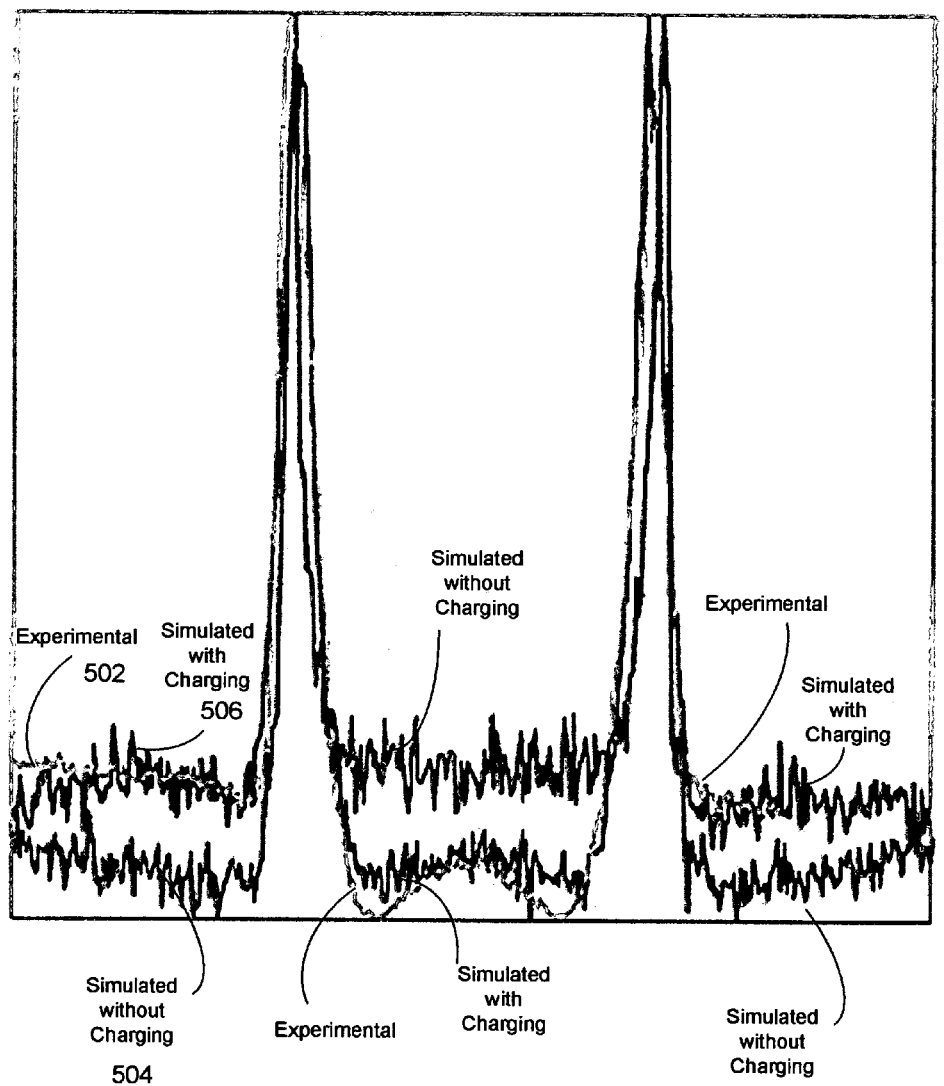
FIG. 5 depicts detected data from across a line as experimentally measured and as simulated without and with charging effects.

In accordance with an embodiment of the invention, the generated mathematical model is configured to account for substrate charging effects. The inventors have determined that the inclusion of substrate charging effects in the modeling substantially improves the accuracy of the modeling. For example, FIG. 5 depicts a line as experimentally measured 502, as simulated without charging 504, and as simulated using a model accounting for charging 506. As seen in FIG. 5, the simulated results using the model with charging 506 is much closer to the experimental measurement 502. The simulation without including substrate charging 504 is too dark outside the line (i.e. outside the two peaks) and is too bright inside the line (i.e. between the two peaks).

The results of the mathematical model generated using the calibration data may be stored in a library of files. If the number of spectra is n, then the library may initially include n files. In one embodiment, the number of library files may be advantageously reduced from n to m (a number less than n) by using principal component analysis. Principal component analysis involves a procedure that transforms a number of correlated variables into a smaller number of principal components. Principal component analysis may receive the library of n files as input and may output eigenfunctions and eigenvalues.

Figure 6B:
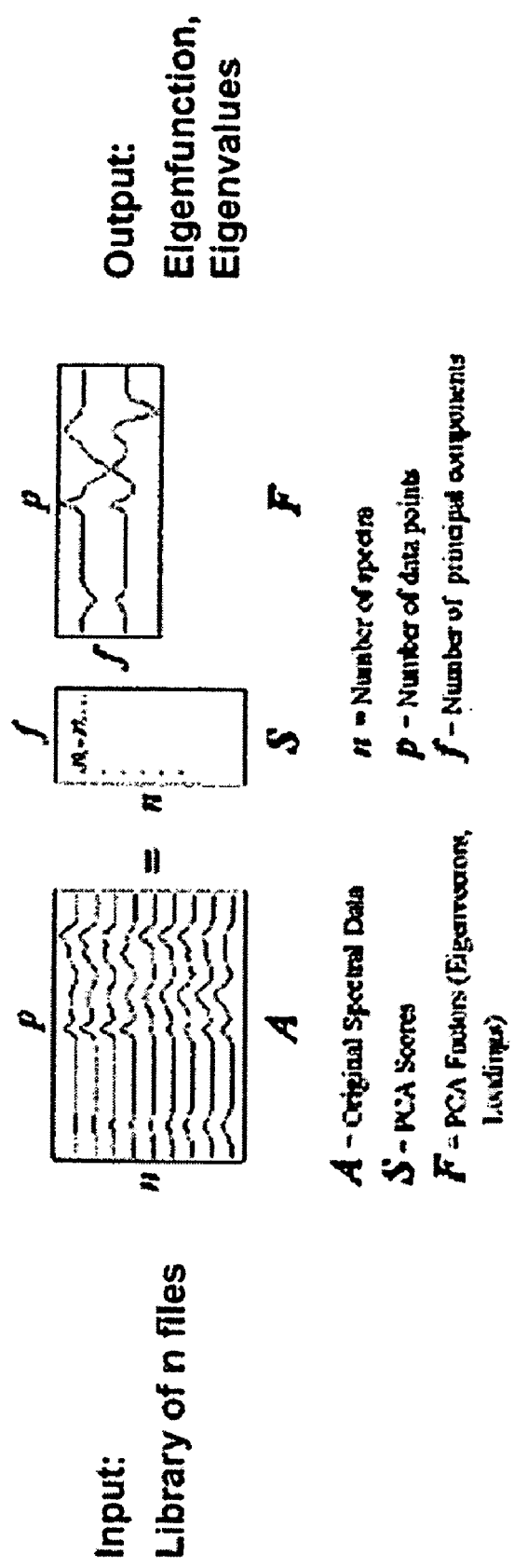

FIGS. 6A and 6B are diagrams depicting principal component analysis (PCA) in accordance with an embodiment of the invention. PCA enables computation of a linear transformation that maps data from a higher dimensional space to a lower dimensional space.

FIG. 6A shows six steps of a mathematical procedure for PCA in accordance with an embodiment of the invention. In a first step, a mean vector (mean function) is calculated from M Nx1 vectors (M N-point functions). In a second step, the mean vector is subtracted from each of the M vectors. In a third step, an N×M matrix is formed, and then a sample covariance matrix C is computed which characterizes the scatter of the data. The fourth and fifth steps comprise computing eigenvalues and eigenvectors of the sample covariance matrix C. In a sixth step, only terms corresponding to the K largest eigenvalues are kept, where K is a number less than M. This sixth step is the dimensionality reduction step.

The diagram of FIG. 6B gives an illustration of what PCA does. The parametrization of the n spectra (A) of p point each comprises determining the f eigenvectors (F) and their f scores (S) for each of the n spectra. In one embodiment, the publicly-available software called ADE-4 is used to implement the PCA parameterization of the scan libraries for our model-based metrology. ADE-4 is freeware developed at the University of Lyon in France.

Figure 7:
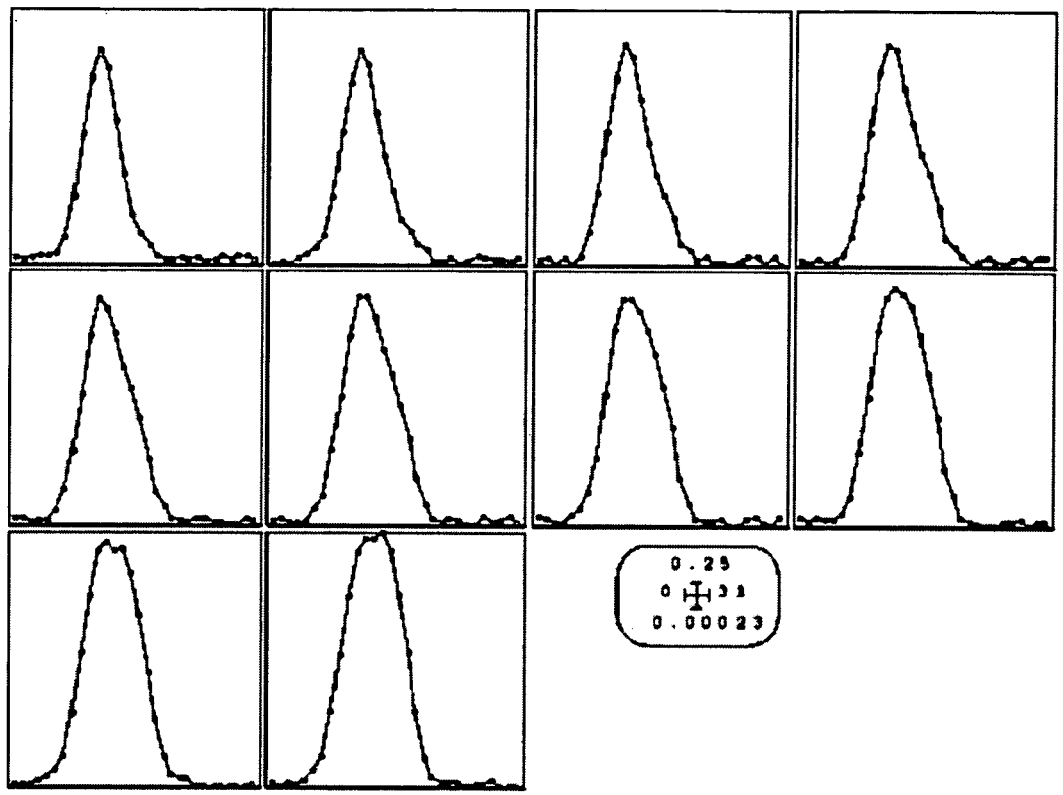
FIG. 7 depicts original signals in an example library of signals in accordance with an embodiment of the invention.

FIG. 7 depicts original signals in an example library of signals in accordance with an embodiment of the invention. In this example, the library of signals comprises two identical Gaussian curves added with different relative weight, from 10% to 100%, in 10% steps. The resultant ten signals in the library are shown in FIG. 7.

Figure 8A:
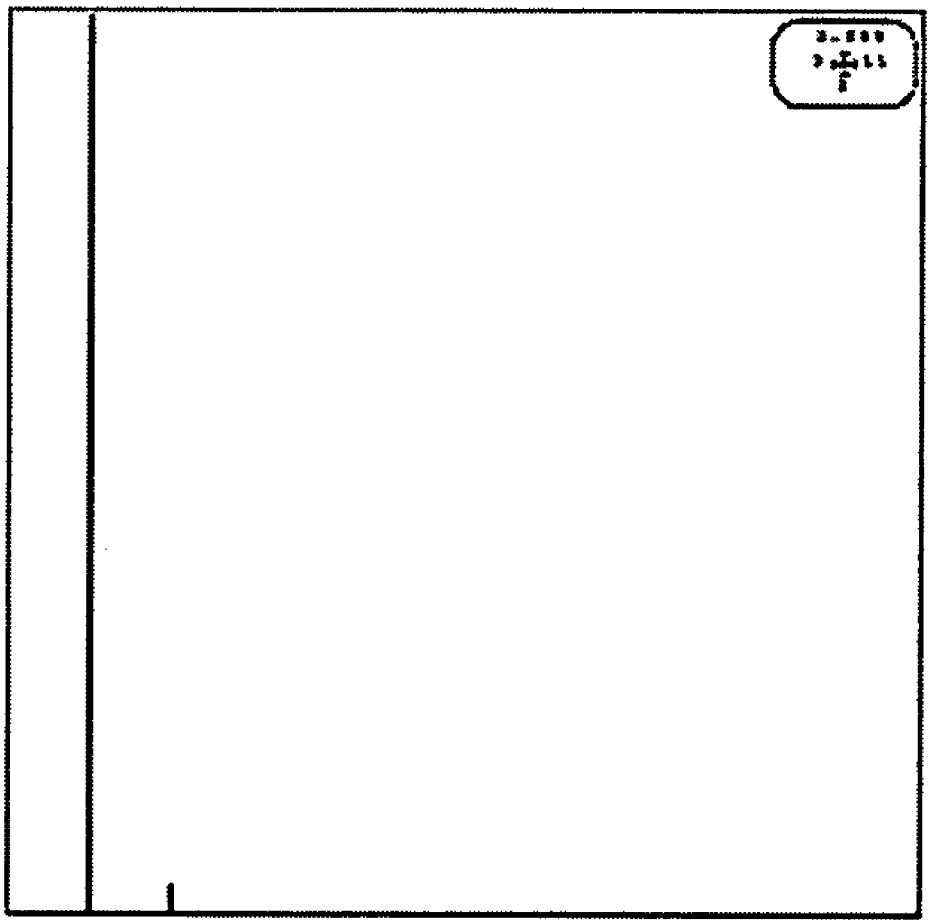
FIG. 8A depicts reported eigenvalues when the PCA is run on column centered standardized data in accordance with an embodiment of the invention.

FIG. 8A depicts reported eigenvalues when the PCA is run on column centered standardized data in accordance with an embodiment of the invention. From FIG. 8A, it is evident that the first two eigenvectors (alternatively, called eigenfunctions) account for most of the variation in the signal. In other words, these two eigenfunctions may be considered as the principal components or principal eigenfunctions.

Figure 8B:
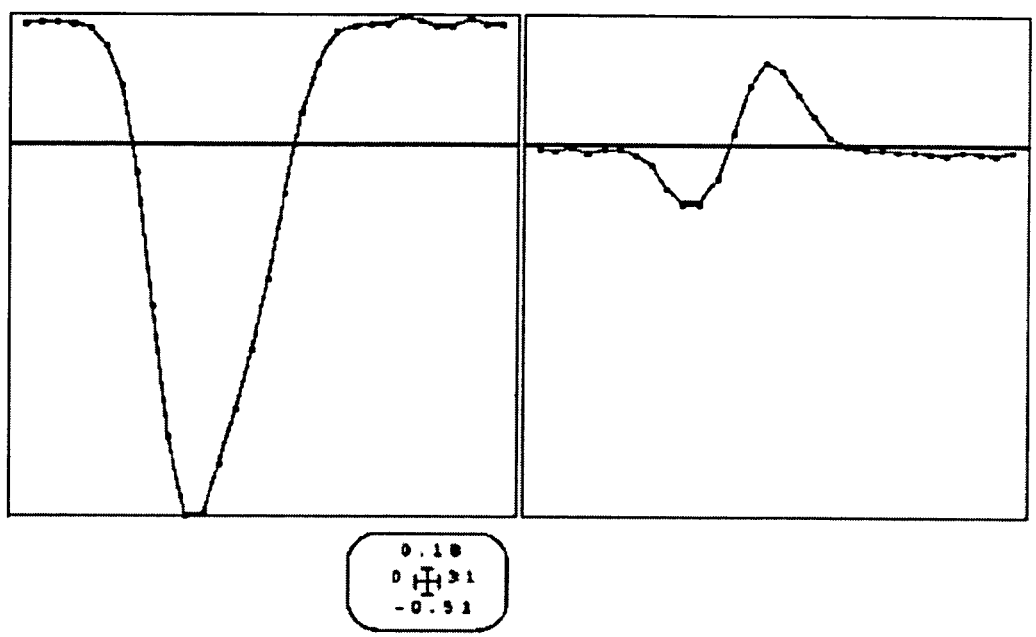
FIG. 8B depicts two estimated eigenfunctions corresponding to the two eigenvalues shown in FIG. 8A.

FIG. 8B depicts two estimated eigenfunctions corresponding to the two eigenvalues shown in FIG. 8A. The leftmost eigenvalue of FIG. 8A is associated with the left eigenfunction of FIG. 8B. The second to the leftmost eigenvalue of FIG. 8A is associated with the right eigenfunction of FIG. 8B.

Figure 9:
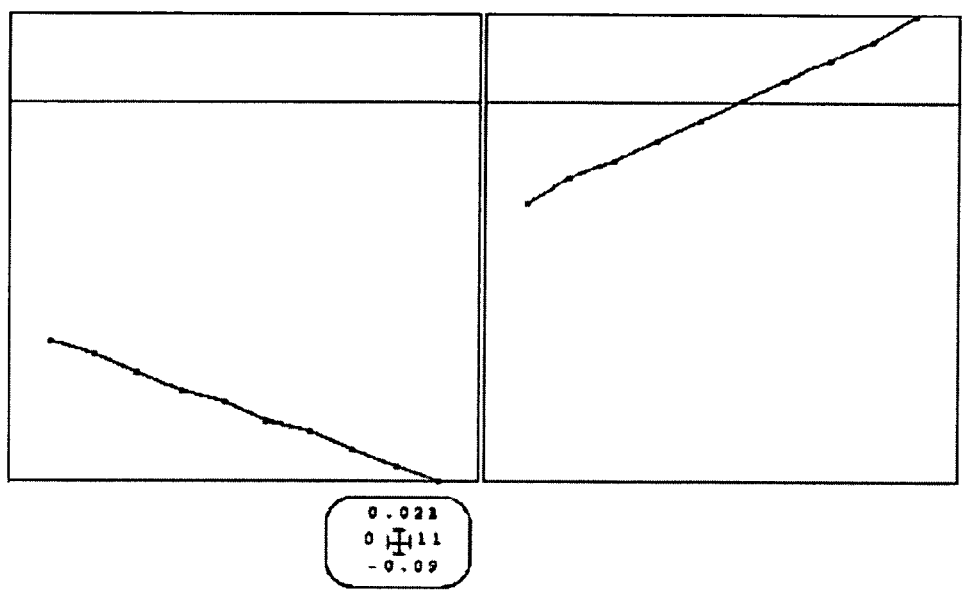
FIG. 9 includes two plots showing the scores for the two eigenfunctions for the set of original signals in the example library in accordance with an embodiment of the invention.

FIG. 9 includes two plots showing the scores for the two eigenfunctions for the set of original signals in the example library in accordance with an embodiment of the invention. The plot on the left shows the scores for the first eigenfunction (on the left in FIG. 8B) for the ten signals in the library. The plot on the right shows the scores for the second eigenfunction (on the right in FIG. 8B) for the ten signals in the library.

Figure 10A:
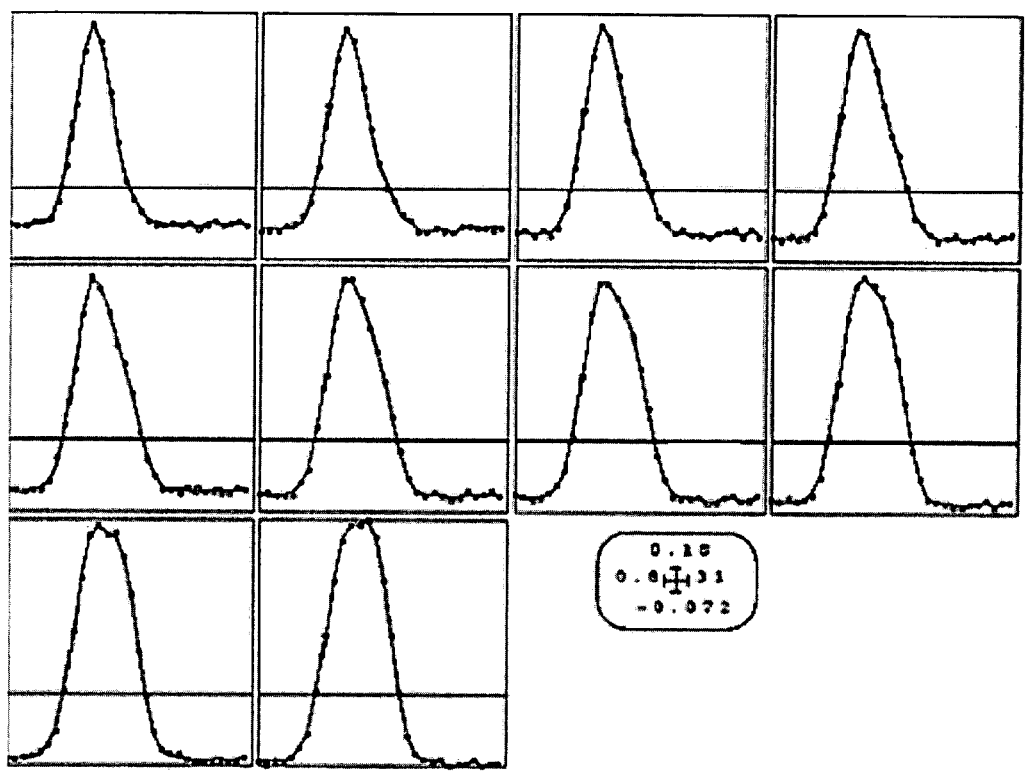
In FIG. 10A, the original signals are compared to the signals modeled by using the eigenfunctions and the scores.

In FIG. 10A, the original signals are compared to the signals modeled by using the eigenfunctions and the scores. The original signals are depicted by the points, and the modeled signals by the lines. As seen from FIG. 10A, the agreement is very good.

Figure 10B:
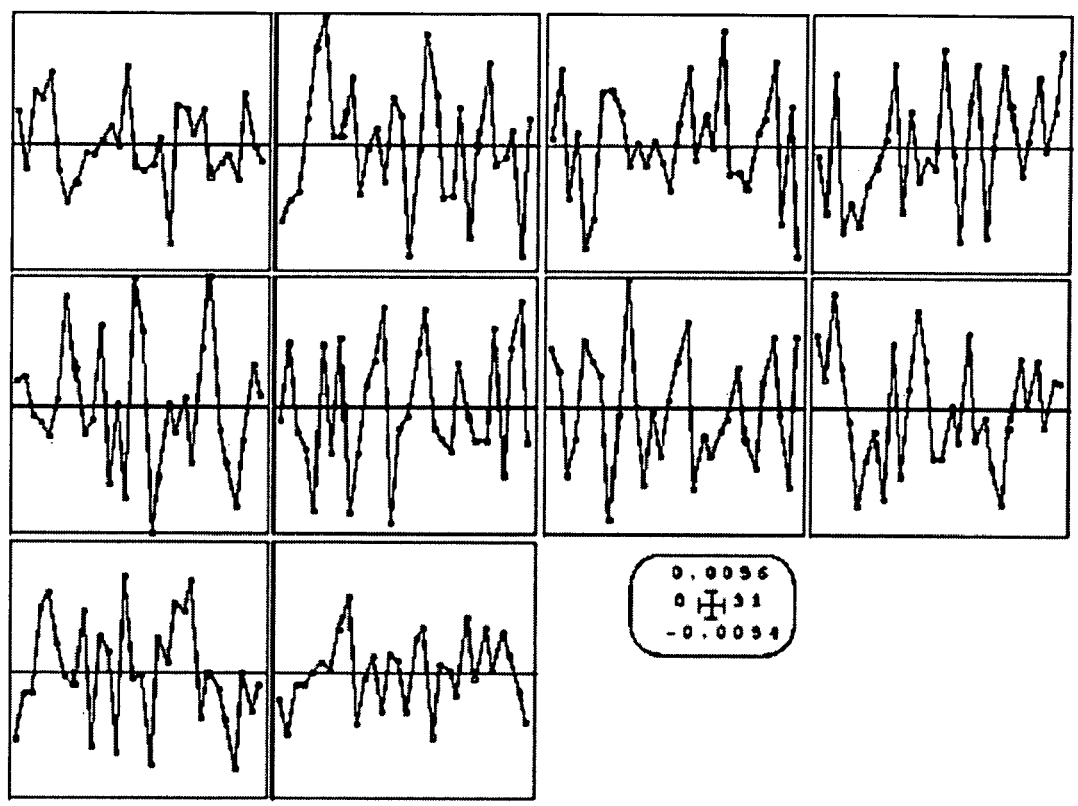
FIG. 10B shows the residuals between the original and modeled signals.

FIG. 10B shows the residuals between the original and modeled signals. Note that the scale of FIG. 10B is significantly magnified in comparison to the scale of FIG. 10A. The noise-like quality of the residuals in FIG. 10B confirms the high quality of the data compression via PCA.

Figure 11:
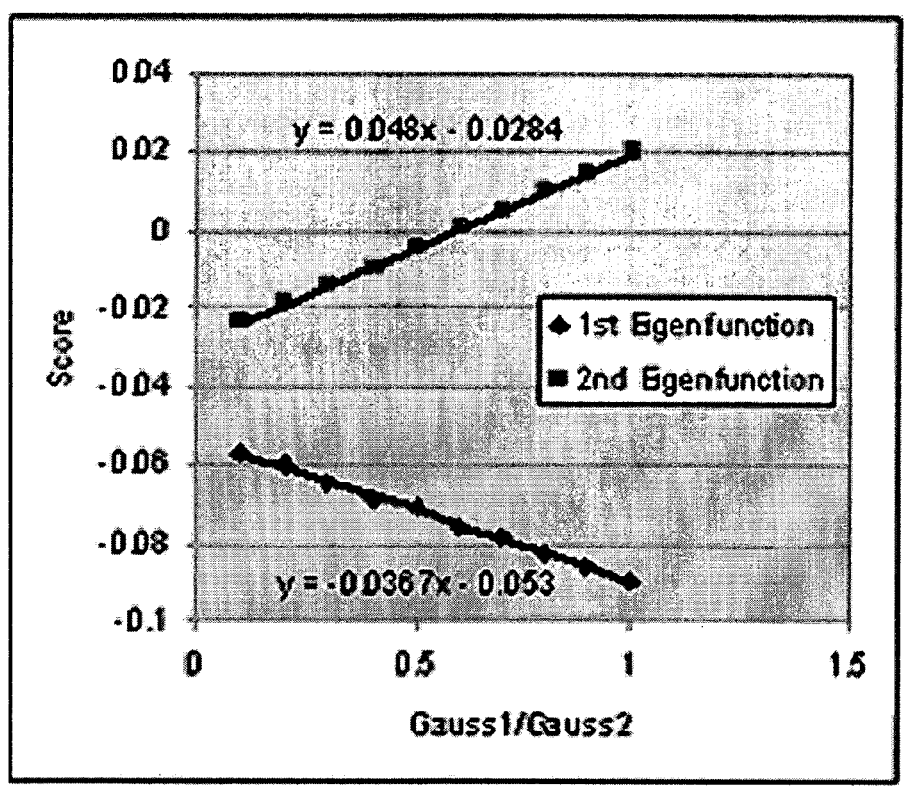
FIG. 11 shows plots of the scores for the two eigenfunctions and linear fits to those in accordance with an embodiment of the invention.

FIG. 11 shows plots of the scores for the two eigenfunctions and linear fits to those in accordance with an embodiment of the invention. In accordance with an embodiment of the invention, such linear fits may be used to effectively expand the reach of the library via extrapolation and/or interpolation. In other words, by using the parameters estimated by the fittings, it is possible to estimate what would be the scores for a signal not present in the library. For example, consider a signal where the first Gaussian (Gauss1) and the second Gaussian (Gauss2) are such that the ratio Gauss1/Gauss2=2. This point is to the right beyond the plotted scores in FIG. 11. Nevertheless, by extrapolating the linear fits, we derive a score of −0.1264 for the first eigenfunction and 0.0596 for the second eigenfunction. By using these extrapolated scores, and the previously computed eigenfunctions, we can model the expected signal.

Figure 12:
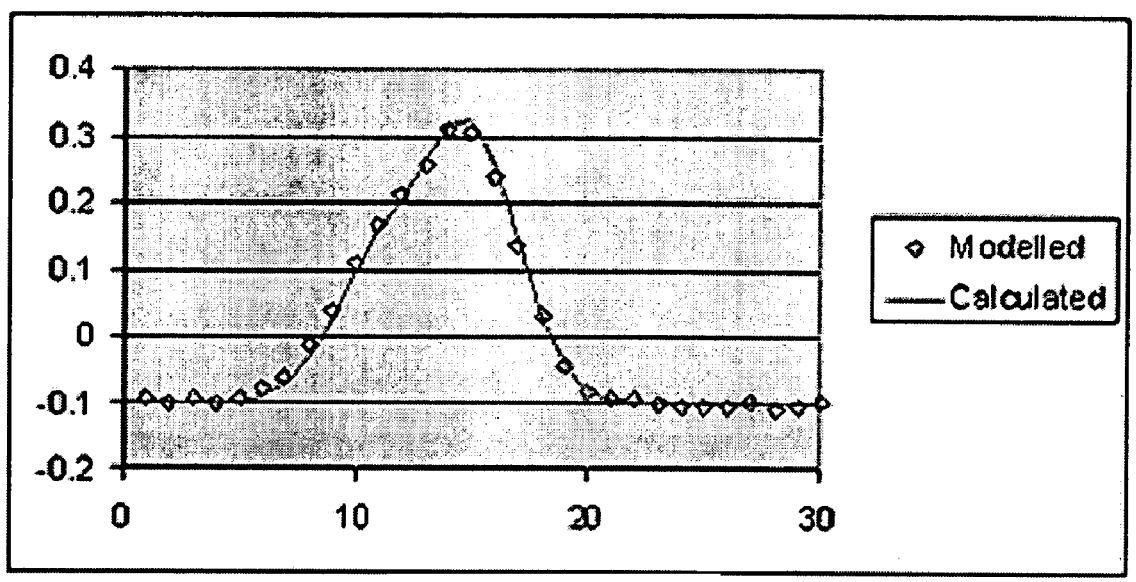
FIG. 12 compares a modeled signal and a calculated signal using extrapolation of the scores in accordance with an embodiment of the invention.

FIG. 12 compares a modeled signal and a calculated signal using extrapolation of the scores in accordance with an embodiment of the invention. As shown by FIG. 12, the modeled and calculated signals match very well, demonstrating excellent results of this procedure.

Figure 13:
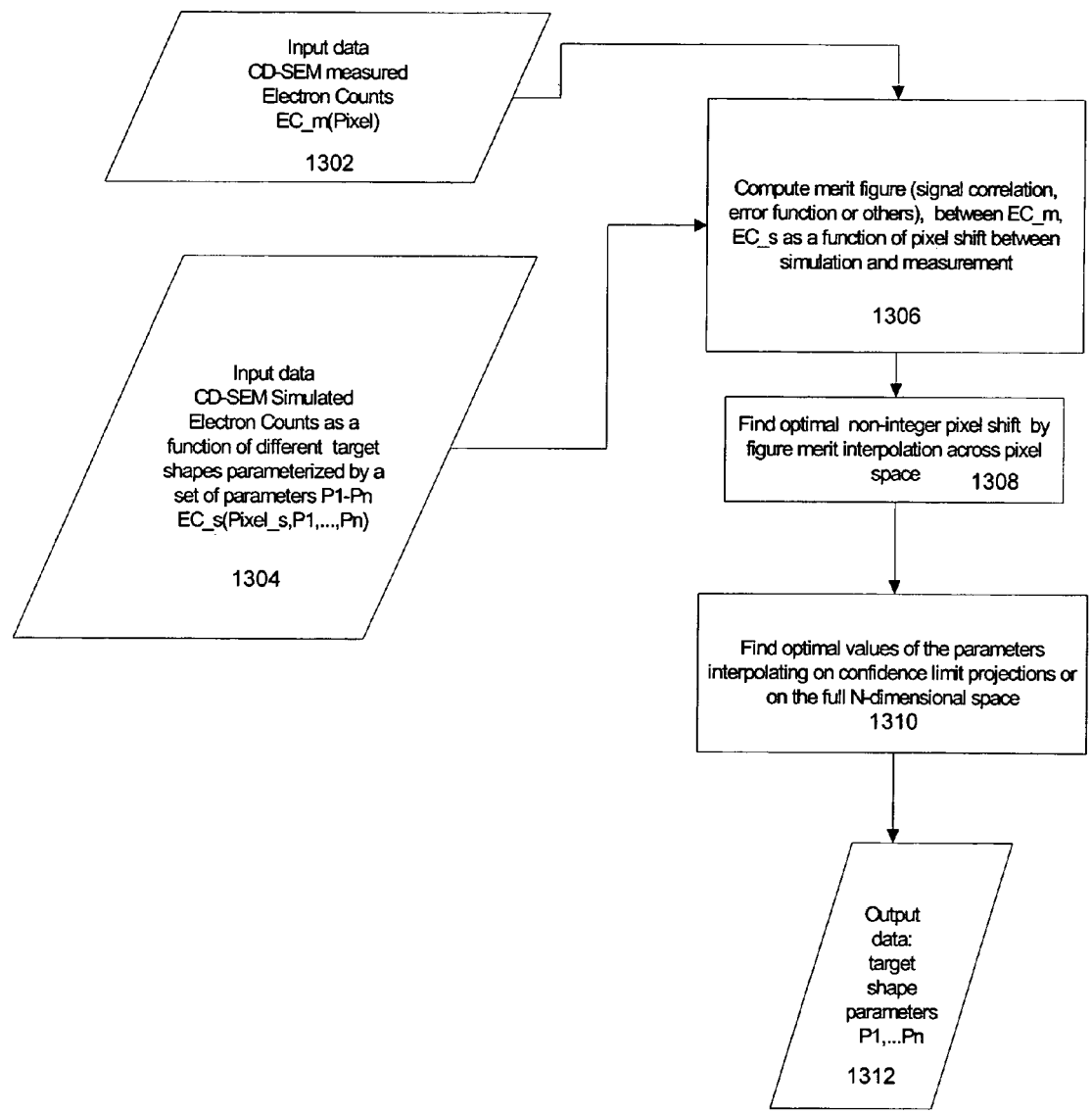
FIG. 13 depicts a flow chart for determining target shape parameters in accordance with an embodiment of the invention.

FIG. 13 depicts a flow chart for determining target shape parameters in accordance with an embodiment of the invention. The cross section of a CD-SEM target is described by a set of parameters $$\vec{P} = (P_0, \ldots, P_n)$$

that completely define its shape. As an example a simple trapezoidal cross section will be uniquely identify by 3 parameters, namely its width, height and sidewall angle. More complex shapes will require a larger set of parameters.

The variation of the cross section is mapped to a hyper-volume in the parameters space $$\vec{P} \in \{(P_{0min}, P_{0max}) \cup \ldots \cup (P_{nmin}, P_{nmax})\}$$

Usually the hyper-volume is sampled discretely. For each set of parameters a simulated CD-SEM scan is produced and stored in the CD-SEM simulation database as a function of the target parameters. Each CD-SEM scan in the database is a function of pixel and of the set of parameters that define a cross section CDscanSIM(pixel, $\vec{P}$).

The experimental CD-SEM scan CDscanMEAS(pixel') 1302 is compared to each of the scans 1304 contained in the simulation database by computing 1306 a figure of merit (signal correlation, MSE, etc. . . . ). In order to compute the figure of merit one has to determine the relation between the simulated scan pixel and the measured pixel. Generally one can assume that, the experimental scan pixel are related to the pixels of the simulated scan by a linear equation pixel=A·pixel'+Offset. The linear equation coefficients (A, Offset) can be found 1308 for each of the simulated signal in the database (i.e. for each target cross section) by computing the figure of merit over a reasonable set of values of A and Offset and, find the values that optimize the figure of merit, and fitting a second order polynomial on a subset of figure of merit data chosen around the optimal.

The interpolated optimal figure of merit is then associated to each of the simulated signal contained in the database. The database can be searched to find 1310 the discrete set of the parameters $\vec{P}$ that optimize the figure of merit. To achieve higher accuracy without increasing the size of the database, various method of interpolation can be used to achieve 'sub-grid' accuracy—the preferred ones being multidimensional interpolation and/or 1d interpolation along the confidence projection. The output data 1312 comprises the target shape parameters.

Figure 14:
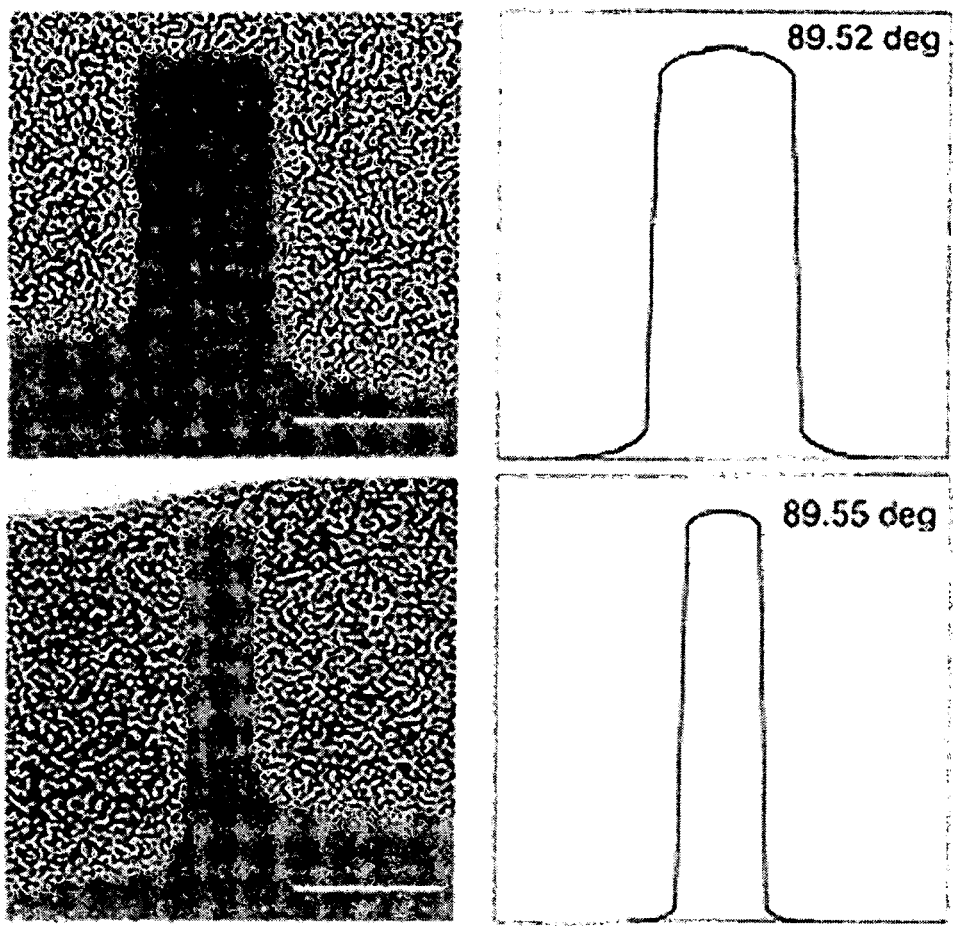
FIGS. 14 and 15 show advantageous results of the invented technique in accordance with an embodiment of the invention.
Figure 15:
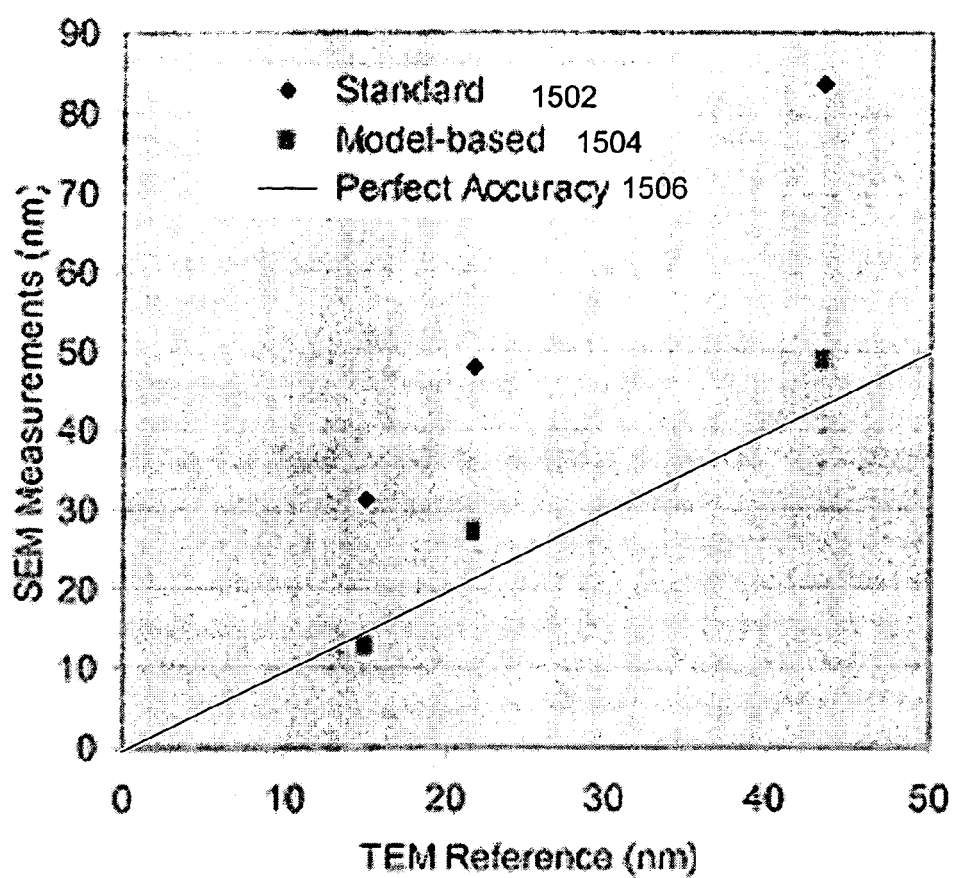

Results of this technique are shown in FIGS. 14 and 15. FIG. 14 shows, on the right side, reconstructed profiles of lines. These profiles were reconstructed from SEM data. The left side of FIG. 14 depicts the profiles as imaged using a TEM technique. One can see that the reconstructed SEM profiles and the imaged TEM profiles match well.

FIG. 15 is a graph depicting conventional SEM measurements 1502 and model-based SEM measurements 1504 of line widths. The model-based measurements 1504 are those performed as described above in accordance with an embodiment of the invention. These measurements are compared against a "perfect accuracy" line 1506 that is based on TEM measurement data. As seen from FIG. 15, the model-based measurements 1504 performed in accordance with an embodiment of the invention is substantially more accurate than the conventional SEM measurements.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for accurate electron beam metrology, the method comprising:
   loading a substrate with a target feature into a scanning electron microscope;
   scanning an electron beam over the target feature;
   detecting scattered electrons from the target feature; and
   measuring a characteristic of the target feature by finding optimal values for parameters of a mathematical model which accounts for substrate charging effects.

2. The method of claim 1, wherein the scanning electron microscope is configured to measure a critical dimension of the target feature.

3. The method of claim 1, wherein the target feature comprises a line lithographically formed on the substrate.

4. The method of claim 1, wherein the target feature comprises a contact hole or via lithographically formed on the substrate.

5. The method of claim 1, wherein the characteristic comprises a line width.

6. The method of claim 1, wherein the characteristic comprises a dimension of a contact hole or via.

7. The method of claim 1, wherein the characteristic comprises profile information of the target feature.

8. The method of claim 1, wherein the mathematical model is implemented using a library of files.

9. The method of claim 1, wherein the library is reduced in size using principal component analysis.

10. The method of claim 9, wherein after the principal component analysis, the library includes a set of principal eigenfunctions and eigenvalues.

11. The method of claim 1, further comprising:
    using interpolation to increase accuracy of the measured characteristic.

12. The method of claim 1, further comprising:
    using extrapolation to increase accuracy of the measured characteristic.

13. The method of claim 1, further comprising a procedure for obtaining calibration data that includes:
    fabricating a calibration sample with multiple measurement sites thereon;
    measuring actual characteristics of the measurement sites using a sufficiently accurate technique;
    loading the calibration sample into a scanning electron beam apparatus;
    scanning an electron beam over the measurement sites;
    detecting scattered electrons from the measurement sites to generate detected data; and
    determining apparent characteristics from the detected data.

14. An apparatus for accurate electron beam metrology, the apparatus comprising:
    an electron source and column assembly for generating and focusing an electron beam;
    a substrate holder for holding a substrate including a target feature;
    scanner components and circuitry for scanning the electron beam over the target feature;
    a detection system for detecting electrons scattered from the target feature; and
    a data processing system for processing data from the detection system,
    wherein the data processing system is configured to measure a characteristic of the target feature by finding optimal values for parameters of a mathematical model which accounts for substrate charging effects.

15. The apparatus of claim 14, wherein the mathematical model is implemented using a library of files.

16. The apparatus of claim 14, wherein the library is reduced in size using principal component analysis.

17. The apparatus of claim 16, wherein after the principal component analysis, the library includes a set of principal eigenfunctions and eigenvalues.

18. The apparatus of claim 14, wherein the data processing system is further configured to use interpolation to increase accuracy of the measured characteristic.

19. The apparatus of claim 14, wherein the data processing system is further configured to use extrapolation to increase accuracy of the measured characteristic.

20. A system for accurate electron beam metrology, the system comprising:
    means for loading a substrate with a target feature into a scanning electron microscope;
    means for scanning an electron beam over the target feature;
    means for detecting scattered electrons from the target feature;
    means for measuring a characteristic of the target feature by finding optimal values for parameters of a mathematical model which accounts for substrate charging effects.

21. The system of claim 20, wherein the database is reduced in size using principal component analysis such that, after the principal component analysis, the mathematical model comprises principal eigenfunctions and eigenvalues.

* * * * *